(12) United States Patent
Aylsworth

(10) Patent No.: US 7,153,271 B2
(45) Date of Patent: Dec. 26, 2006

(54) METHOD AND SYSTEM FOR DIAGNOSING CENTRAL VERSUS OBSTRUCTIVE APNEA

(75) Inventor: Alonzo C. Aylsworth, Wildwood, MO (US)

(73) Assignee: Airmatrix Technologies, Inc. MO (US)

( * ) Notice: Subject to any disclaimer, the term of this patent is extended or adjusted under 35 U.S.C. 154(b) by 0 days.

(21) Appl. No.: 11/123,371

(22) Filed: May 6, 2005

(65) Prior Publication Data

US 2005/0261600 A1 Nov. 24, 2005

Related U.S. Application Data

(60) Provisional application No. 60/573,015, filed on May 20, 2004.

(51) Int. Cl.
*A61B 5/08* (2006.01)

(52) U.S. Cl. .................. 600/538; 600/529; 600/534
(58) Field of Classification Search .................... None
See application file for complete search history.

(56) References Cited

U.S. PATENT DOCUMENTS

| | | | | |
|---|---|---|---|---|
| 5,704,345 A | * | 1/1998 | Berthon-Jones | 128/204.23 |
| 5,803,066 A | * | 9/1998 | Rapoport et al. | 128/204.23 |
| 6,599,252 B1 | * | 7/2003 | Starr | 600/532 |

* cited by examiner

*Primary Examiner*—Robert L. Nasser
(74) *Attorney, Agent, or Firm*—Mark E. Scott; Conley Rose, P.C.

(57) ABSTRACT

A method and related system for diagnosing central versus obstructive apnea. Some of the illustrative embodiments may be a method comprising sensing minute undulations of airflow through one or more airways of a patient during an apnea event, and diagnosing obstructive apnea based on the minute undulations.

13 Claims, 3 Drawing Sheets

METHOD AND SYSTEM FOR DIAGNOSING CENTRAL VERSUS OBSTRUCTIVE APNEA

CROSS-REFERENCE TO RELATED APPLICATIONS

This specification claims the benefit of provisional application Ser. No. 60/573,015, filed May 20, 2004, and titled "Method and system for diagnosing central versus obstructive apnea," which application is incorporated by reference herein as if reproduced in full below.

STATEMENT REGARDING FEDERALLY SPONSORED RESEARCH OR DEVELOPMENT

Not applicable.

BACKGROUND OF THE INVENTION

1. Field of the Invention

Various embodiments are directed to methods and systems for determining whether an apnea event is caused by central or obstructive difficulties.

2. Description of the Related Art

Sleep apnea is defined in the field of respiratory therapy as a cessation of breathing during sleep lasting ten seconds or more. Sleep apnea may be characterized as either "central apnea" or "obstructive apnea." Obstructive apnea is so named because the cessation of breathing is caused by an obstruction in the respiratory tract. For example, portions of the soft palate may collapse blocking the airway. In the case of obstructive apnea, the patient may attempt to inhale (i.e. has breathing effort), but the blockage prevents such an inhalation. Central apnea occurs when a sleeping person's central nervous system fails to instruct the diaphragm to retract to draw air into the lungs.

When a person is diagnosed with sleep apnea, a physician may need to determine whether the apnea is central or obstructive. In the related art, this determination may require the patient to make an overnight stay in a sleep diagnostic lab where numerous sensors and electrodes are placed on the patient. One of the key sensors used to determine whether breathing effort is present is a chest band. If breathing effort accompanies an apnea event then the patient has obstructive apnea. On the other hand, if no breathing effort corresponds with an apnea event, then it is most likely that the patient has central apnea.

While diagnosing central versus obstructive apnea in this fashion may be viable, it is a cumbersome process requiring the person to sleep in an unfamiliar environment coupled to a plurality of sensors and electrodes that are in most cases uncomfortable for the patient. Moreover, utilizing a sleep lab to diagnose central versus obstructive apnea can be very expensive, costing anywhere between $2,000 and $3,000 for an overnight study as of the time of this writing.

Thus, what is needed in the art is a method and related system to diagnose central versus obstructive apnea without the difficulties and expense associated with a sleep diagnostic lab environment.

SUMMARY OF SOME OF THE EMBODIMENTS

The problems noted above are solved in large part by a method and related system for diagnosing central versus obstructive apnea. Some of the illustrative embodiments may be a method comprising sensing minute undulations of airflow through one or more airways of a patient during an apnea event, and diagnosing obstructive apnea based on the minute undulations.

Other illustrative embodiments may be a system comprising a processor and a sensor electrically coupled to the processor (wherein the sensor is configured to fluidly couple to a breathing airway of a patient, and wherein the sensor senses airflow through the breathing airway). The processor is configured to make a determination of whether the patient suffers from central or obstructive apnea based at least in part on airflow sensed during an apnea event.

Yet other illustrative embodiments may be a method comprising providing a test device to a patient, providing a cannula to the patient (wherein the cannula fluidly couples to the test device), having the patient wear the cannula coupled to the test device during sleep in the patient's home, recording respirations of the patient during sleep by the test device comprising at least one apnea event to create a recorded apnea event, and diagnosing one of central or obstructive apnea by the test device based on the recorded apnea event.

Yet still other illustrative embodiments may be a system comprising a means for executing programs, a means for sensing an attribute of airflow electrically coupled to the means for executing (wherein the means for sensing is configured to fluidly couple to a means for interfacing to a patient's). The means for executing records airflow during an apnea event of a patient as measured by the means for sensing, and wherein the means for executing uses the recorded apnea event to diagnose whether the patient suffers from central or obstructive apnea.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "connect" or "connects" is intended to mean either an indirect or direct connection. Thus, if a first device connects to a second device, that connection may be through a direct connection, or through an indirect connection via other devices.

The term "cannula" refers to a respiratory mask (either full or partial) that fluidly couples one or more of a patient's airways to a testing device. Thus, a "nasal cannula" couples at least one naris to the test device. Likewise, an "oral cannula" may couple to a patient's mouth. The word "cannula" alone could thus refer to a nasal cannula, an oral cannula, or a cannula that couples to both a patients nose and mouth.

DETAILED DESCRIPTION OF THE PREFERRED EMBODIMENTS

Figure 1:
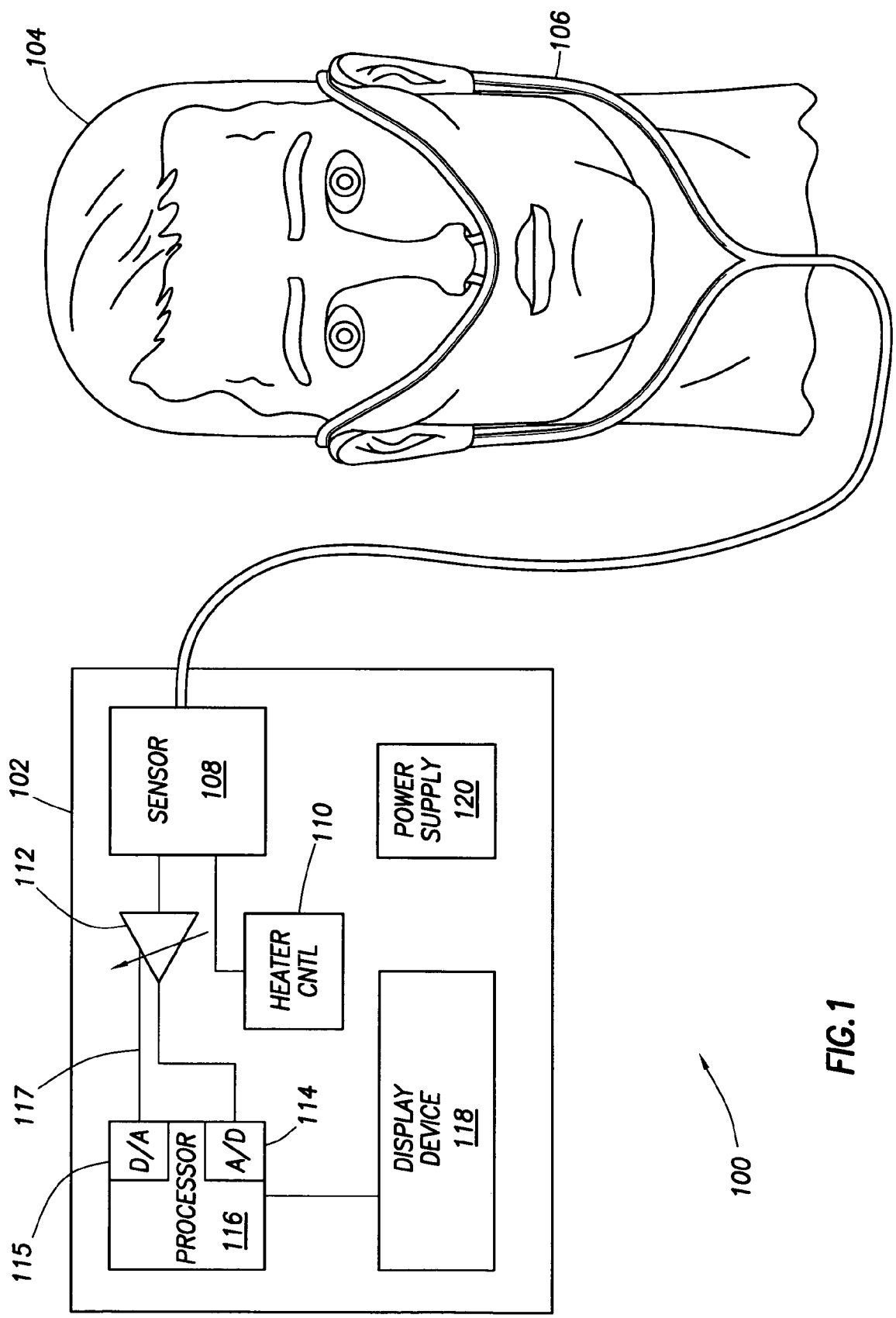
FIG. 1 illustrates a cannula-based central versus obstructive apnea diagnostic system in accordance with some embodiments of the invention.

FIG. 1 illustrates a system for diagnosing central versus obstructive apnea. In particular, the system may comprise a test device 102 coupled to a patient 104 by way of an illustrative cannula 106. The test device 102, in accordance with at least some embodiments of the invention, may comprise a sensor 108 coupled to the cannula 106. In the embodiments illustrated in FIG. 1, the cannula 106 is a single lumen nasal cannula, and therefore only one sensor 108 may be needed. In alternative embodiments of the invention, the cannula 106 may be a bifurcated nasal cannula, with an individual fluid flow path to each naris, and in these embodiments an additional sensor may be utilized in the test device 102. In yet still other embodiments, the cannula 106 may be nasal mask, e.g., a mask that covers the nose or a mask that seals to one or both nares by way of nasal pillows.

In accordance with at least some embodiments of the invention, the sensor 108 may be a mass flow sensor available from Microswitch (a division of Honeywell Corp.) having a part number AWM92100V. However, other sensors, such as high accuracy pressure sensors, may be equivalently used. The Microswitch flow sensor operates on the principle of a heated element within the air stream that experiences different cooling effects depending on the volume of the airflow. Thus, in these embodiments the test device 102 may also comprise a heater control circuit 110 responsible for controlling the heat applied to the heated element within the sensor 108.

The test device 102 may also comprise an amplifier 112 which couples a signal between the sensor 108 and an analog-to-digital (A/D) converter 114 of a processor 116. Depending on the type of sensor used, amplifier 112 may not be needed. In accordance with at least some embodiments of the invention, sensor 108 may produce an output signal that has an attribute that changes proportional to the amount of airflow through the flow sensor. In other embodiments, sensor 108 may produce an output signal that has an attribute that changes proportional to sensed pressure changes, such as pressure associated with airflow through the monitored breathing orifice. Any attribute of an electrical signal may be used, such as frequency, phase, electrical current flow, or possibly a message-based system where information may be coded in message packets. In some embodiments the sensor 108 produces an output signal whose voltage is proportional to the airflow through the sensor. As discussed more fully below with respect to FIG. 2, the amplifier 112 may have a variable gain so that the processor 116 may selectively increase and decrease the gain of amplifier 112, such as by applying a particular control voltage to the amplifier 112, generated by the digital-to-analog converter 115 and applied across line 117.

As illustrated in FIG. 1, the test device 102 may comprise a processor 116. In some embodiments, the processor 116 may be a microcontroller, and thus has an on-board converter A/D 114, D/A converter 115, on-board random access memory (RAM) (not shown), read only memory (ROM) (not shown) as well as other on-board circuits, such as circuits that allow the processor 116 to communicate to external devices. The processor illustrated in the embodiments of FIG. 1 could be a Cypress MicroSystems device having a part number CY8C26643. While a microcontroller having many of the on-board components is preferred, the test device 102 may be implemented using an individual processor, AD, D/A, RAM, ROM, and the like.

Still referring to FIG. 1, the test device 102 may further comprise an indicator or display device 118 coupled to the processor 116. While the display device may take many forms, in accordance with some embodiments of the invention the display device may comprise a liquid crystal display (LCD), such as an LCD display part number TM320240DFG1 available from TIAN-MA Microelectronics Company.

The test device 102 may further comprise a power supply 120. In accordance with at least some embodiments of the invention, the power supply 120 is capable of taking alternating current (AC) power available at a wall outlet and converting it to one or more direct current (DC) voltages for use by the various electronics within the system. In alternative embodiments where the test device 102 is portable, the power supply 120 may have the capability of switching between converting the AC wall power to DC, or drawing current from on-board or external batteries, and converting to voltages needed by the devices within the test device 102. In yet further embodiments, the power supply 138 may be external to the test device 102.

The various embodiments of the invention were developed in the context of sensor 108 being a flow-through or mass flow sensor. Thus, the remaining discussion of operation of the various embodiments is in relation to sensor 108 being a mass flow sensor. However, the discussion is equally applicable to a test device 102 using a pressure sensor, where the pressure sensor senses pressure fluctuations associated with airflow into or out of the a breathing orifice, including pressure fluctuations associated with small wisps of airflow or minute undulations (discussed more thoroughly below).

As the patient 104 inhales, at least a portion of the airflow into the nostrils is drawn through the cannula 106. Because the cannula 106 fluidly couples to the sensor 108, a portion of the air inhaled by the patient 104 is thus sensed by the sensor 108. In accordance with at least some embodiments of the invention, the test device 102 stores waveforms (e.g., flow as a function of time) while the patient sleeps, and more particularly during an apnea event. The stored waveforms may be used to diagnosis the type of apnea experienced by the patient. Alternatively, the test device 102 may itself may make a diagnosis based on the waveform (either in real time or by analysis of the stored waveform) to determine whether the patient 104 suffers from central or obstructive apnea.

Figure 2:
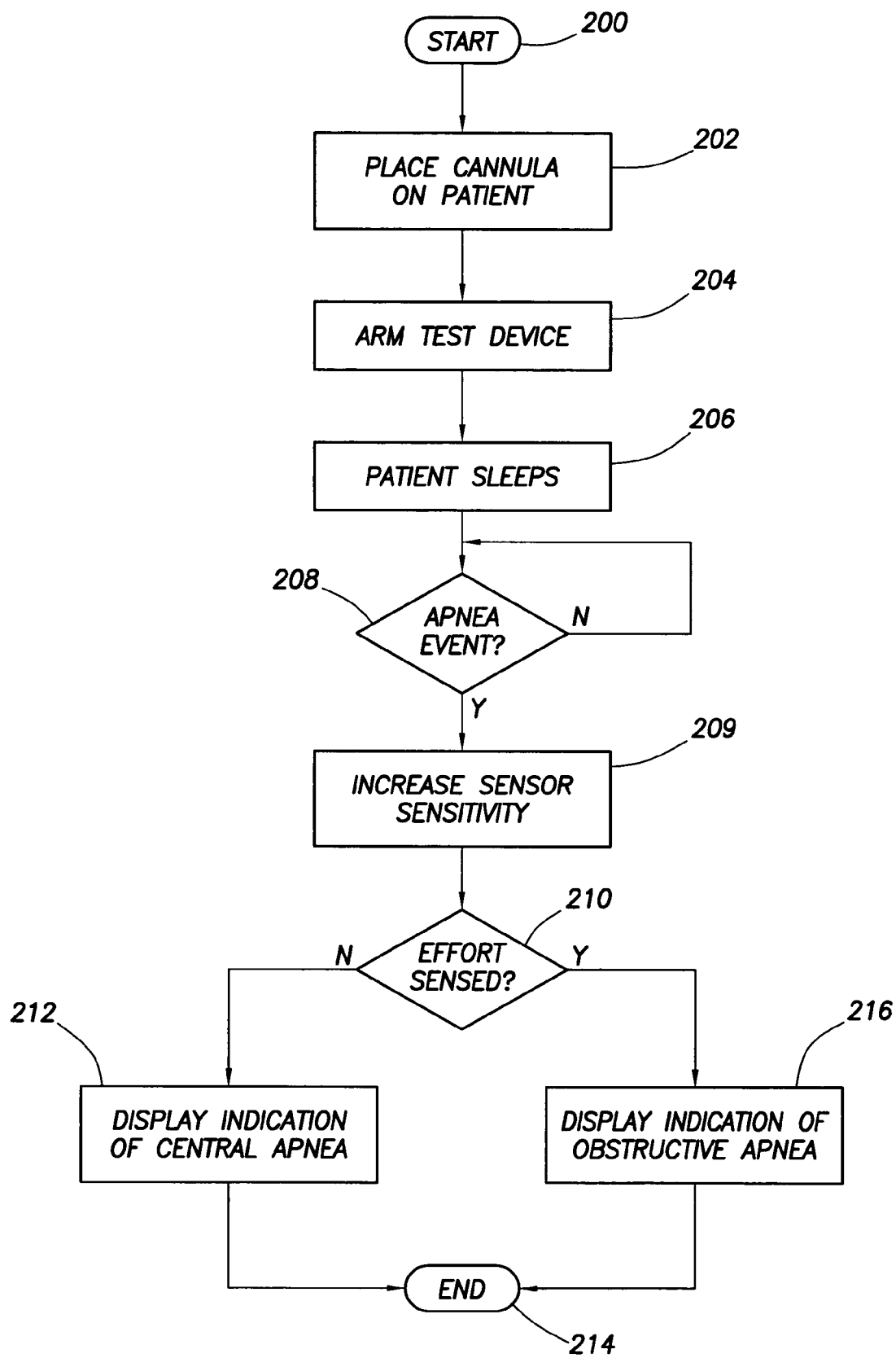
FIG. 2 illustrates a method that may be implemented by the test device of FIG. 1 to diagnose central versus obstructive apnea in accordance with embodiments of the invention.

FIG. 2 illustrates a method in accordance with embodiments of the invention. In particular, the process starts (block 200), and proceeds to placing the cannula on the patient (block 202). Thereafter, the test device 102 is armed (block 204), and the patient allowed to sleep (block 206). As the patient sleeps, the test device 102 monitors the patient's breathing pattern searching for apnea events (block 208). As discussed above, an apnea event may be defined in the respiratory care field as a cessation of breathing for ten seconds or more. However, the apnea events monitored by the test device 102 may be shorter or longer as desired. Skipping for now block 209, when an apnea event is detected, the test device 102 determines whether effort is sensed during the apnea (block 210). In accordance with some embodiments of the invention, effort may be sensed by small wisps of airflow or minute undulations in the sensed airflow during the apnea event, and thus the 'cessation' of airflow indicative of an apnea event need not be a complete cessation. In some embodiments, after detecting the presence of an apnea event (block 208), the illustrative system of FIG. 1 may increase the sensitivity of the sensor 108 (block 209) such that the small wisps of airflow or minute undulations are more easily sensed. Increasing the sensitivity of the sensor may involve increasing the gain of illustrative amplifier 112 and/or decreasing the full scale range readable A/D converter 114.

Figure 3:
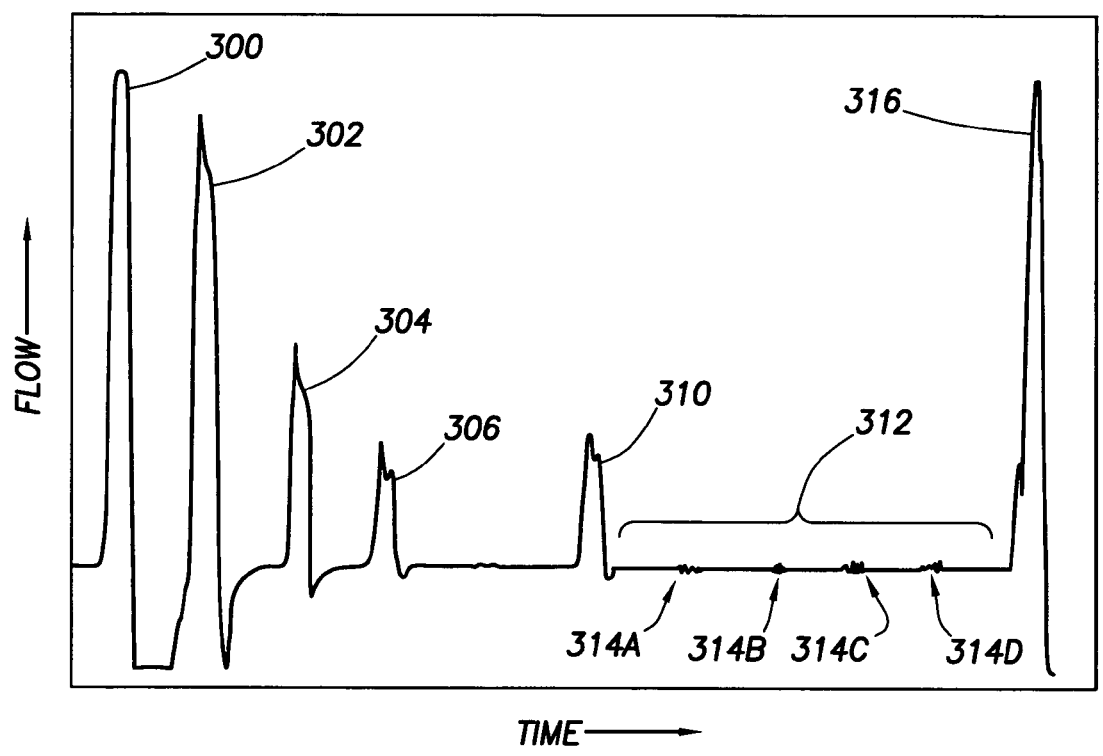
FIG. 3 is an illustrative waveform of patient respirations exhibiting obstructive apnea indications.

Although the Applicant of the present specification does not wish to be tied to any particular theory of the physiology behind operation of the device, it is believed that in the case of obstructive apnea that as the patient's central nervous system stimulates movement of the diaphragm, small wisps or volumes of air may be drawn into the lungs past and/or around the obstruction, and these small wisps or volumes of air may be sensed by the sensor (discussed more fully with respect to FIG. 3). Alternatively or in additional to the theory of small wisps of air bypassing the obstruction, movement of the diaphragm may also act to deflect the fatty tissue causing the obstruction, and the deflection itself may cause a small volumes or minute undulations of airflow through the patient's airways even though no air reaches the lungs. In cases where the small wisps or minute undulations of air are not sensed, this may be indicative of a situation where the patient's central nervous system did not command an inhalation.

Returning to FIG. 2, if no effort is sensed, the test device 102 may display an indication of central apnea (block 212) and the process may end (block 214). Conversely, if effort is sensed, the test device 102 may display an indication of an obstructive apnea (block 216), and the process may end (block 214). It is noted that the display of the indication of central or obstructive apnea may not take place immediately at its detection, and rather the information may be stored in volatile or non-volatile memory (not shown) within the test device for later display.

FIG. 3 illustrates a flow versus time waveform as may be measured by a test device 102 in accordance with embodiments of the invention. In particular, FIG. 3 illustrates several inhalations of the patient by flow peaks 300, 302, 304, 306 and 310. Notice how the height of the peaks drops over time. This drop over time is characteristic of an oncoming apnea event, however an apnea may take place at any time. There is an extended period of time illustrated by bracket 312 where there are no major breathing events, and if this extended period of time is greater than ten seconds, then this breathing event may be defined as an apnea. However, within the period time 312 there are shown several small wisps or minute undulations of airflow 314. It is these small wisps or minute undulations of airflow that the inventor of the present specification has found are indicative of obstructive apnea. In other words, these wisps or minute undulations of airflow represent an effort on the part of the patient to inhale, yet an obstruction somewhere in the respiratory tract substantially prevents inhalation. As the patient's blood oxygen saturation begins to drop, the patient's brain wakes the patient, at least to some extent, and a large breath is taken, as indicated by peak 316.

Figure 4:
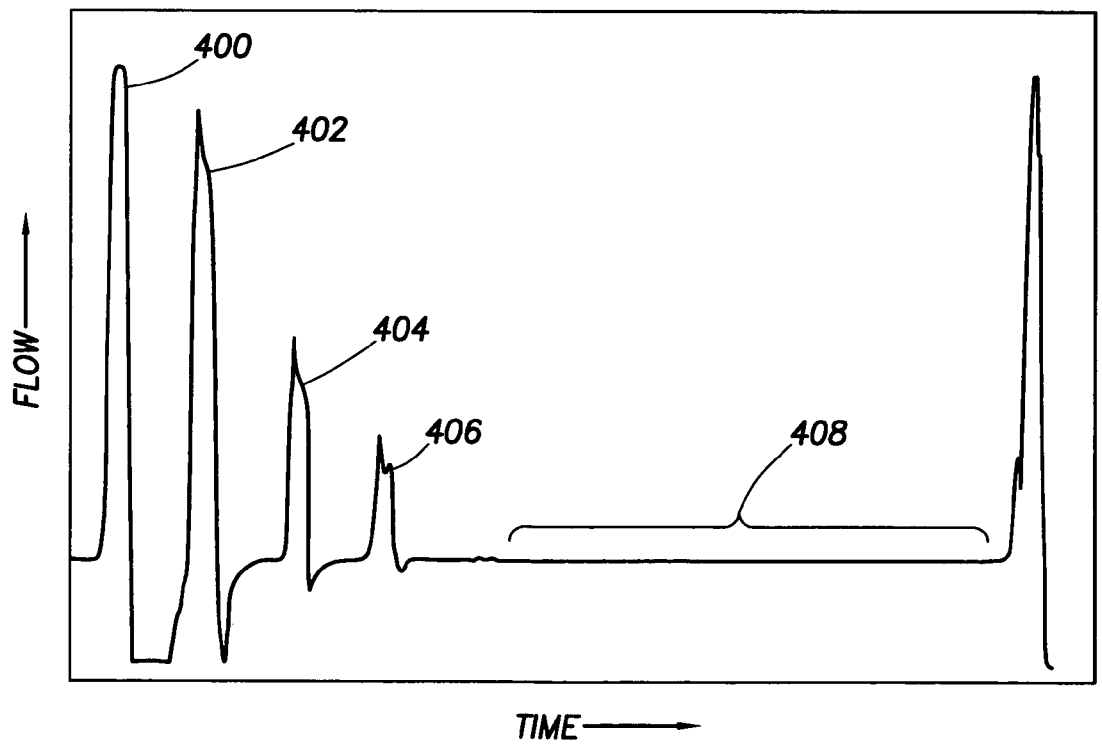
FIG. 4 is an illustrative waveform exhibiting a patient's respiration in central apnea conditions.

FIG. 4 illustrates a waveform of flow as a function of time as may be measured by a test device 102. In particular, FIG. 4 illustrates the characteristic inhalation peaks with decreasing volumes at peaks 400, 402, 404 and 406. However, within the period of time illustrated by bracket 408, an apnea event occurs yet no wisps or minute undulations of airflow are detected by the flow sensor. Thus, while the period of time represented by bracket 408 may be representative of an apnea event, because the flow sensor 108 senses no effort on the part of the patient to inhale, this illustrative apnea event is central apnea.

Referring again to FIG. 3, the various peaks illustrating illustrations 300–306 show a regular or rhythmic breathing pattern. In accordance with some embodiments of the invention, the test device 102 may anticipate the next inhalation of the patient, and increase the sensitivity of one or more of the sensor 108, the amplifier 112 and/or the A/D converter 114 to enable the test device 102 to more accurately detect effort on the part of the patient. The small wisps or minute undulations detected in the case of obstructive apnea may be relatively small, e.g. approximately one 200th of the volume of a full inhalation, such as illustrated by peak 300.

As long as the patient breathes exclusively through the nose, a nasal cannula may suffice to sense the small wisps or minute undulations of airflow. However, in some circumstances a patient may mouth breath, and thus alternative embodiments the cannula may also fluidly couple to the patient's mouth. The cases where both the mouth and nose are monitored, test device 102 may comprise an additional sensor for the oral airway, or all the monitored airways may couple to a flow sensor.

Because the test device 102 may be relatively small and battery powered, and further because the diagnosis of central versus obstructive apnea may be done by way of a cannula, the embodiments of the present invention may be utilized within a patient's home. Moreover, the test may be performed under more normal sleeping conditions (without sensors, wires, and electrodes coupled to the patient) and at significantly less cost than a full sleep study commissioned in a sleep lab.

It is intended that the following claims be interpreted to embrace all such variations and modifications.

What is claimed is:

1. A system comprising:
   a processor; and
   a sensor electrically coupled to the processor, wherein the sensor is configured to fluidly couple to a breathing airway of a patient, and wherein the sensor senses airflow through the breathing airway;
   wherein the processor is configured to make a determination of whether the patient suffers from central or obstructive apnea based on presence of minute undulations of airflow through the breathing airway at periods of time when inhalations of the patient are expected.

2. The system as defined in claim 1 wherein the minute undulations are approximately $\frac{1}{200}^{th}$ of the volume of a normal, rhythmic inhalation during a sleep state of the patient.

3. The system as defined in claim 1 wherein the processor is configured to record airflow sensed during the apnea event for later diagnosis.

4. The system as defined in claim 1 wherein the processor diagnoses central apnea based on a substantially complete lack of airflow through the breathing airway at periods of time when inhalations of the patient are expected.

5. The system as defined in claim 1 wherein the sensor further comprises a mass flow sensor.

6. The system as defined in claim 5 wherein the sensor further comprises a Microswitch mass flow sensor having part No. AWM92100V.

7. The system as defined in claim 1 wherein the sensor further comprises a pressure sensor.

8. A system comprising:
   a processor; and a sensor electrically coupled to the processor, wherein the sensor is configured to fluidly couple to a breathing airway of a patient, and wherein the sensor senses airflow through the breathing airway;

wherein the processor is configured to make a determination of whether the patient suffers from central or obstructive apnea based at least in part on airflow sensed during the apnea event; and wherein the processor is configured to increase sensitivity of the sensor during periods of time when inhalations of the patient are expected.

9. A system comprising:

a means for executing programs; and a means for sensing an attribute of airflow electrically coupled to the means for executing programs, wherein the means for sensing configured to fluidly couple to a means for interfacing the patient to the means for sensing;

wherein the means for executing records airflow during an apnea event of the patient as measured by the means for sensing, and wherein the means for executing uses the recorded apnea event to diagnose whether the patient suffers from central or obstructive apnea; and wherein the means for executing diagnoses obstructive apnea based on presence of minute airflow undulations through the nares at periods of time when inhalations of the patient are expected.

10. The system as defined in claim 9 wherein the minute airflow undulations are approximately $1/200^{th}$ of the volume of a normal, rhythmic inhalation during a sleep state of the patient.

11. The system as defined in claim 9 wherein the means for executing diagnoses central apnea based on a substantially complete lack of airflow through the nares at periods of time when inhalations of the patient are expected.

12. The system as defined in claim 9 wherein the means for sensing further comprises a means for sensing at least a portion of the patients respiratory airflow.

13. The system as defined in claim 9 wherein the means for sensing further comprises a means for sensing pressure associated with the patient's respiratory airflow.

* * * * *